(12) United States Patent
Carlin et al.

(10) Patent No.: US 8,601,877 B2
(45) Date of Patent: Dec. 10, 2013

(54) METHOD AND DEVICE FOR ULTRASONIC MEASUREMENTS

(75) Inventors: Carl-Gustaf Carlin, Tyresö (SE); Erik Thomas Bergkvist, Stockholm (SE); Lars Rickard Eriksson, Stockholm (SE); Jarl-Olof Huldén, Solna (SE)

(73) Assignee: Atlas Copco Industrial Technique Aktiebolag, Stockholm (SE)

( * ) Notice: Subject to any disclaimer, the term of this patent is extended or adjusted under 35 U.S.C. 154(b) by 226 days.

(21) Appl. No.: 13/260,604

(22) PCT Filed: Mar. 26, 2010

(86) PCT No.: PCT/SE2010/000074
§ 371 (c)(1),
(2), (4) Date: Sep. 27, 2011

(87) PCT Pub. No.: WO2010/110716
PCT Pub. Date: Sep. 30, 2010

(65) Prior Publication Data
US 2012/0017686 A1 Jan. 26, 2012

(30) Foreign Application Priority Data
Mar. 27, 2009 (SE) ...................... 0900391

(51) Int. Cl.
*G01N 29/28* (2006.01)

(52) U.S. Cl.
USPC ................. 73/644; 73/600; 73/632

(58) Field of Classification Search
USPC ................. 73/644, 599, 600, 618, 629, 632
See application file for complete search history.

(56) References Cited

U.S. PATENT DOCUMENTS

| 4,530,143 | A | * | 7/1985 | Casarcia .................... 29/407.02 |
| 4,760,740 | A | * | 8/1988 | Meisterling .................... 73/761 |
| 5,226,327 | A | * | 7/1993 | Fassina .......................... 73/761 |
| 5,343,785 | A | * | 9/1994 | Holt et al. .................... 81/57.38 |
| 6,138,512 | A | * | 10/2000 | Roberts et al. .................... 73/570 |
| 6,615,663 | B2 | * | 9/2003 | Kenney et al. .................. 73/632 |
| 2001/0035050 | A1 | | 11/2001 | Kenney et al. |

FOREIGN PATENT DOCUMENTS

GB    2109555 A    6/1983

OTHER PUBLICATIONS

International Search Report dated Jun. 28, 2010 issued in International Appln. No. PCT/SE2010/000074.

* cited by examiner

*Primary Examiner* — J M Saint Surin
(74) *Attorney, Agent, or Firm* — Holtz, Holtz, Goodman & Chick, PC

(57) ABSTRACT

An ultrasonic measurement device and method in which an ultrasonic transducer is acoustically coupled to an object to be measured by a resilient material contact layer. The transducer transmits a plurality of consecutive ultrasonic transmit signals into the object being measured, the transmit frequency of each of the plurality of transmit signals being distinct from the frequency of the other transmit signals of the plurality of transmit signals. Signal echoes of the transmitted signals are received, and based on the received signal echoes, at least one transmit frequency to be used for ultrasonic measurement of the object is selected.

13 Claims, 7 Drawing Sheets

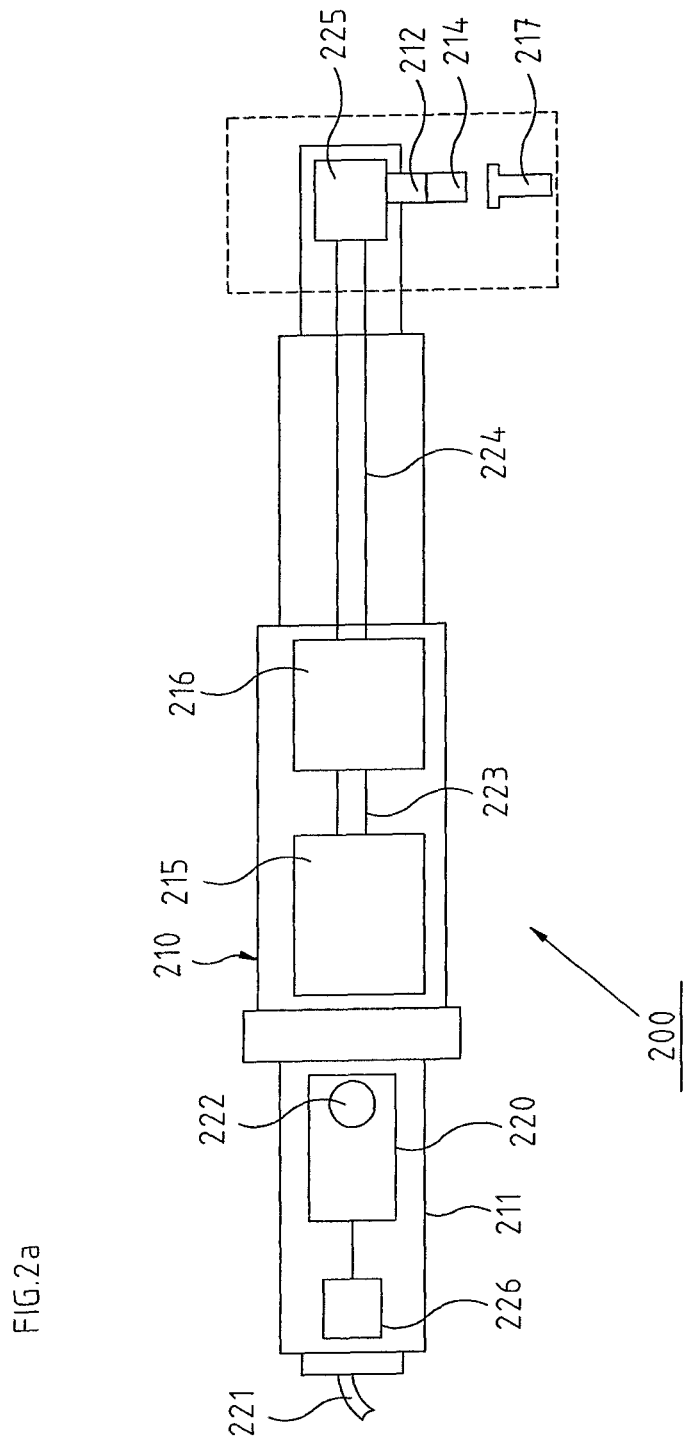

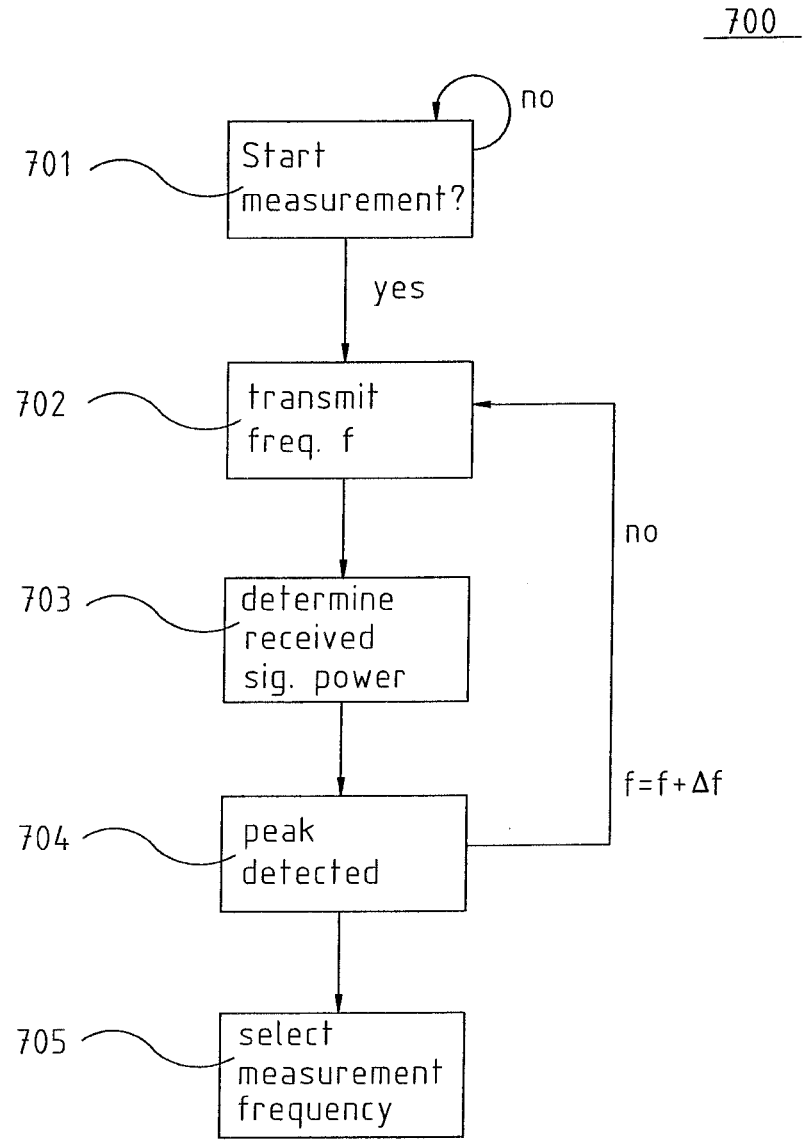

METHOD AND DEVICE FOR ULTRASONIC MEASUREMENTS

This application is a U.S. National Phase Application under 35 USC 371 of International Application No. PCT/SE2010/000074, filed Mar. 26, 2010.

FIELD OF THE INVENTION

The present invention relates to ultrasonic measurement, e.g. in devices for tightening fasteners to a desired tightening force. In particular, the present invention relates to an ultrasonic measurement method according to the preamble of claim 1. The present also relates to an ultrasonic measurement device according to the preamble of claim 10.

BACKGROUND OF THE INVENTION

The increasing requirement of quality control and efficiency in assembly plants such as manufacturing plants has resulted in the development of sophisticated assembly tools. For example, with regard to the tightening of joints, threaded fasteners, such as nuts, screws or bolts, often have to be rotated a number of turns until a desired tightening force finally has been reached.

The strength of such joints is related to the force by which the fastener holds the two (or more) joint parts together. Therefore, it is of major importance that fasteners of such joints are tightened to such extent that it can be ensured that required tightening force levels are reached. However, even though the sophisticated tools used today provide various methods of ensuring that a desired minimum tightening force of a joint is also in fact reached during the tightening process, e.g. by measuring the torque applied by the tool and the duration of the torque in terms of angular rotation, uncertainties regarding the actual tightening force that has been reached still exist, e.g. due to the fact that the friction between the fastener and the one or more components being joined can vary substantially from joint to joint.

This problem has been addressed by various more or less sophisticated solutions. For example, the dimension of the fastener actually being used can be increased with respect to the theoretical requirement of the dimension of the fastener, thereby ensuring that even if the fastener of larger dimension is not tightened to maximum tightening force, it can still be ensured that the fastener is tightened at least to the extent that is required by the particular design.

According to another solution, the tightening of the fastener is followed by a measurement of the elongation the fastener is subject to during the fastening process. Such measurement is often carried out by a device utilizing ultrasonic technology, and the tightening force can be calculated from the elongation of the fastener resulting from the tightening process. Such use of ultrasonic technology requires that the (length of the) fastener is first measured beforehand, i.e. when the fastener is still in an unstressed state, and then after the fastening process is finished in order to determine the elongation.

Such ultrasonic measurement, however, requires acoustic contact between the transducer that is used to impose ultrasonic sound waves into the fastener, which in turn results in it being difficult to perform measurement during the actual fastening process. The measurement is therefore in general performed after the fastening has been completed, which reduces to a large extent the advantage of using high-speed fastening tools in the fastening process, since the time it takes to perform the ultrasonic measurement inherently will substantially exceed the amount of time it takes to perform the actual fastening.

Therefore, use of ultrasonic measurement is sparsely used in situations in which fast assembly is desired and/or required, and instead being used in situations where the tightening force is of greater importance that the speed at which the tightening is being carried out.

Consequently, there exists a need for a method that allows ultrasonic measurement during a fastening process, without substantially affecting the assembly time.

Further, ultrasonic measurements are useful not only in fastening processes but also various other kinds of situations, e.g. in determination of inhomogeneities in materials/objects, and there exists a need for an improved method of obtaining acoustic contact between measurement device and material/object in a convenient manner, while at the same time ensuring satisfactory signal-to-noise-ratios with regard to the received signal.

SUMMARY OF THE INVENTION

It is an object of the present invention to provide an ultrasonic measurement method and an ultrasonic measurement device that at least mitigates the above-mentioned problems. This object is achieved by a method according to the characterizing portion of claim 1, and a device according to the characterizing portion of claim 11, respectively.

According to the invention, it is provided an ultrasonic measurement method wherein an ultrasonic transducer is acoustically coupled to an object to be measured by means of a resilient material contact layer. The transducer transmits a plurality of consecutive ultrasonic transmit signals into the said object being measured, the transmit frequency f of each of said plurality of transmit signals being distinct from the transmit frequency f of the other transmit signals of said plurality of transmit signals. Signal echoes of said transmit signals are received, and based on the said received signal echoes, at least one transmit frequency f to be used for ultrasonic measurement of the said object is selected.

This has the advantage that a method is provided that is capable of increasing reflected signal levels in systems utilising a contact layer of a material having a ultrasonic signal propagation speed that substantially differs from the material/object to be measured, since it has been realized that the portion of the originally transmitted power that is reflected back to the transducer to a large extent depends on the actual frequency of the signal being transmitted.

Further characteristics of the present invention, and advantages thereof, will be evident from the following detailed description of preferred embodiments and appended drawings, which are given by way of example only, and are not to be construed as limiting in any way.

BRIEF DESCRIPTION OF THE DRAWINGS

FIGS. 2A-B shows a fastener tightening tool according to an embodiment of the present invention.

FIG. 7 shows an exemplary method according to the present invention.

DETAILED DESCRIPTION OF EXEMPLARY EMBODIMENTS

As was mentioned above, a common method of joining components during an assembly or manufacturing process is to use threaded fasteners to obtain a suitable clamping force. As was also mentioned above, the accuracy of the tightening (clamping) force of such joints can be verified by measuring the elongation that the fastener is subjected to during the fastening process, e.g. using ultrasonic technology. Measurement of elongation can be used to obtain a considerably more accurate measurement of the tightening force as compared to e.g. when measuring the torque and angle of rotation applied by the assembly tool.

Figure 1:
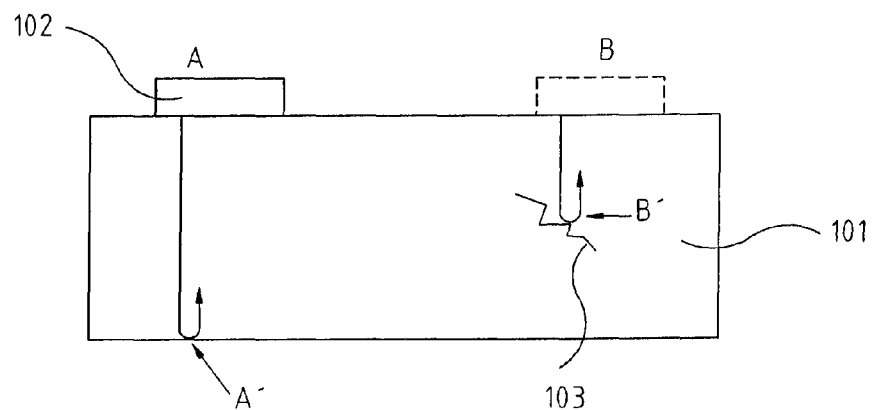
FIG. 1 schematically shows an ultrasonic measurement principle.

Ultrasonic measurement has found use in various different areas of technology, and typically a sound wave is generated which penetrates the subject to be measured, whereafter a reflected portion of the transmitted sound wave is measured. The reflection is then used to obtain a measurement of the particular feature that is of interest. Apart from fastener tightening, ultrasonic measurement can be used, e.g., in finding defects within an object, such as cracks that are not visible from the outside. The basic principle of ultrasonic measurement is disclosed in FIG. 1, in which a material 101 is measured by means of a transducer 102.

With regard to such measurement processes, the object, e.g. material 101, is subjected to a transmit pulse or short transmit burst by means of the transducer 102, which is connected to the fastener at a location A. (Part of) the transmitted pulse (burst) will then be reflected at the other end, location A' of the material and return to the transducer (the transducer can be of such kind that it is used both to transmit and receive the ultrasonic signals or, alternatively, a separate receiver can be used to receive the reflected signals), and by detecting the reflected signal, lengths can be measured and compared by comparing the reflections (echoes) of two or more transmitted signals. If the material 101 is not homogeneous, and e.g. contains a crack 103, the transmitted signal, at a measurement location B, will be reflected at the crack location B' and thereby return in a shorter period of time as compared to the signal transmitted at location A. If the time between transmission of the signal and the reception of the echo signal is measured, the distance to the crack in the material can be calculated.

With regard to elongation of fasteners during a fastener tightening process, an echo received after a completed fastening process is compared to an echo received prior to the commencing of the fastening process, whereby the elongation can be calculated from the comparison.

However, if such measurement method is to be used, it is desired if not required that a good acoustic contact is obtained between the transducer and the object to be measured from a signal transmission point of view so that a high enough portion of the transmitted power is not only properly transferred to the object to be measured, but also properly returned to the transducer.

If the transducer is not in direct contact with the fastener, and, e.g. there is an air-gap in between the transducer and the fastener, most of the power transmitted from the transducer will be reflected already at the air-object boundary, so that no or only a little portion of the transmitted energy actually reaches the object to be measured. Further, most of the fraction of energy that actually reaches the object, and is reflected at the opposite end of the object, will also be reflected at the end facing the transducer so that only a very little or no portion of transmitted power will be properly reflected and returned to the transducer.

Therefore, in order to ensure quality measurements, it is of major importance that a satisfactory acoustic contact between transducer and object to be measured can be obtained. This can, for example, be accomplished by applying glycerine onto the object and then press the transducer against the fastener whereby the glycerine ensures that no air-gap in the transducer-object coupling is present.

Although being appropriate in solutions where the ultrasonic measurement is used in non-time-critical applications, use in time-critical applications, such as often is the case in e.g. fastener tightening processes in product assembly lines, use of glycerine or other suitable liquids as a contact medium is difficult or impossible to combine with the desire of fastener tightening tools having built-in transducer.

Therefore, a solution to the problem of achieving a satisfactory acoustic coupling between transducer and fastener during a tightening process is to simply integrate the transducer into the fastener, e.g. each fastener is provided with a transducer. This solution, however, inherently gives rise to undesired costs.

According to the present invention, however, it is provided a measurement device having a built-in transducer and which despite the built-in transducer still can ensure a satisfactory acoustic coupling between transducer and fastener. This is accomplished by means of a coupling layer for acoustically coupling the transducer to the object to be measured which is integrated in the device and which consists of a resilient material.

This has the advantage that as the measurement device arranged to abut an object to be measured, the resilient coupling layer will ensure that a satisfactory acoustic coupling between transducer and fastener is obtained, and hence allow ultrasonic measurement in a convenient manner, e.g., with regard to fastener tightening, during a tightening process.

The present invention will now be exemplified more in detail with reference to an exemplary method of usage wherein the measurement device is a fastener tightening tool.

Figure 2B:
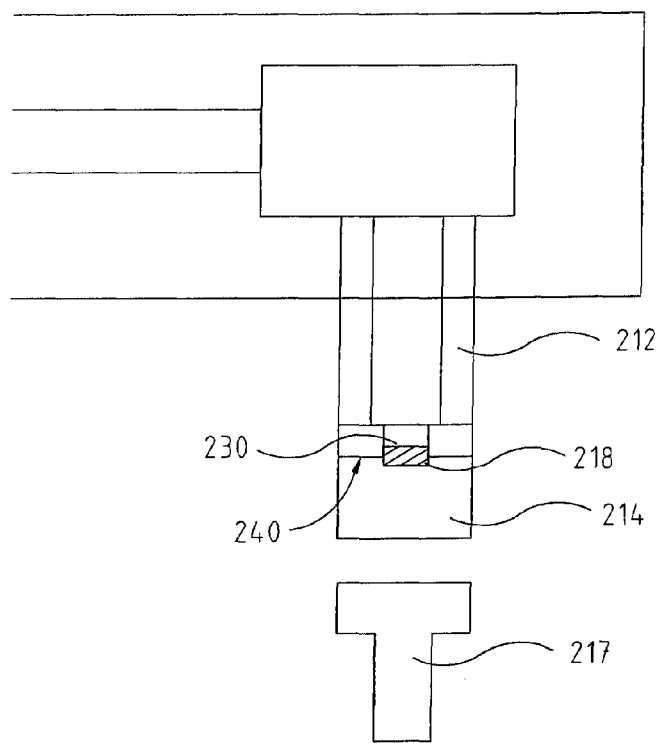

In FIGS. 2A-B is schematically shown a device 200 in the form of an electric assembly tool according to an exemplary embodiment of the present invention. The device 200 consists of a housing 210, part of which constituting a rear handle 211 for being gripped, in use, by a device operator. Within the housing 210 there is an electric motor 215 which is power supplied by means of an external power source via a cable 221 (in an alternative embodiment, the electric motor is, instead, power supplied by one or more batteries located within the housing 210).

The device 200 further comprises a motor output shaft 223, which is connected to a gearing 216 so as to enable a fastener to be driven by the device 200 at a rotational speed being different from the rotational speed of the motor 215. Further, a gearing output shaft 224 extends from the gearing 216 into angle gear 225 having an output shaft 212, which is arranged to carry a socket 214, fixedly or attachable thereto, for releasable connection with a fastener 217 to be tightened. The socket 214 can be of any known type that can be used for rotational fastening, e.g. square, polygonal. The socket is preferably replaceable so as to allow fastening of fasteners having different dimensions.

The portion indicated by dashed lines is shown more in detail in FIG. 2B. The end of the socket 214 facing away from a fastener to be fastened is provided with a central hole so as to allow a resilient contact layer 218 to contact the fastener via the hole. The contact layer 218 is in connection with a transducer 230, e.g. permanently fixed thereto in order to ensure proper acoustic contact between contact layer and transducer. As can be seen from the figure, the shaft 212 extending from the angular drive 225 and which rotates the socket 214 is a hollow shaft 212 which encloses the resilient contact layer 218 and the transducer 230 so as to allow the transducer 230 and contact layer 218 to remain stationary during the tightening process.

In this exemplary embodiment, the transducer 230 is used both to generate ultrasonic signals and as a sensor to measure signal echoes. With regard to the contact between the contact layer 218 and the fastener 217, this contact should be releasable in order to allow fast switch to the next fastener once a current fastener has been tightened. Therefore the contact layer 218 is arranged such that it extends through the central hole of the socket 214 and slightly extends past the surface 240 of the socket 214 that abuts the fastener 217 during the fastening process. This will result in a slight compression of the resilient contact layer during the fastening process, thereby imposing a spring force that act on the surface of the fastener 217 so that proper contact between the contact layer and the fastener can be ensured. The extent to which the contact layer extends through the hole of the socket should be kept small, e.g., in the range 0.1-1 mm, although other ranges is possible and depend e.g. on the particular material from which the contact layer is produced. The contact layer can, for example, have a thickness in the range 0.1-5 mm.

If the contact layer extends too far into the socket 214 the compression of the contact layer will, although giving rise to a high spring force ensuring good contact, compress the contact layer to such extent that the properties of the contact layer may change and thereby impose uncertainties in transducer measurements. In general, the contact layer should preferably be produced from a material having a known approximate transmittance, e.g. silicon.

Although the above "dry-coupling" solution provides a method of ensuring reliable acoustic contact from transducer to fastener it still has some drawbacks. Even if the ultrasonic signal propagation speed in the resilient material is considerably higher than in air, e.g. 1000 m/s, it is still low when compared to the sound propagation speed in metal (e.g. 5-6000 m/s). This means that due to the differences in propagation speeds, a large portion of the signal energy, e.g. in the order of 9/10 of the total energy transmitted from the transducer will be reflected already at the contact layer-fastener boundary. Further, when the remainder (i.e. 1/10 of the transmitted energy) of the signal has been reflected at the other end of the fastener there is yet another unfavourable reflection when the signal enters the contact layer from the fastener, again reducing the signal power to e.g. 1/10 of the remainder of the signal. Consequently, the signal energy of the echoed signal once reaching the transducer, can be as low as 1% of the signal originally transmitted by the transducer, which imposes difficulties attempts to correctly interpret the received signal due to e.g. low signal-to-noise-ratio.

According to the present invention, however, it is provided a method that is capable of increasing reflected signal levels in systems of the above kind. This is accomplished by determining a transducer transmit frequency which is advantageous from a reflection point of view. It has been realized that the portion of the originally transmitted power that is reflected back to the transducer to a large extent depends on the actual frequency of the signal being transmitted.

Figure 3A:
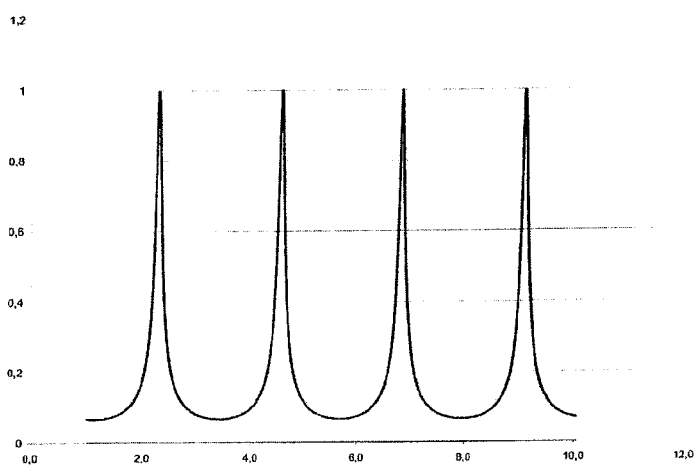
FIGS. 3A-C show examples of amplitude variations of received echo signals as a function of transducer frequency.
Figure 3B:
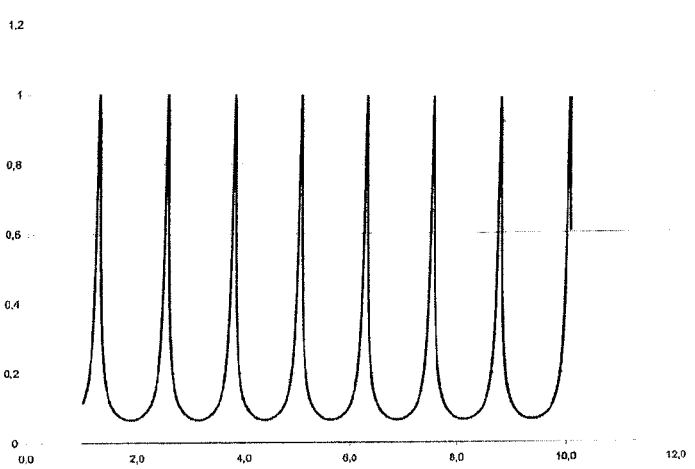
Figure 3C:
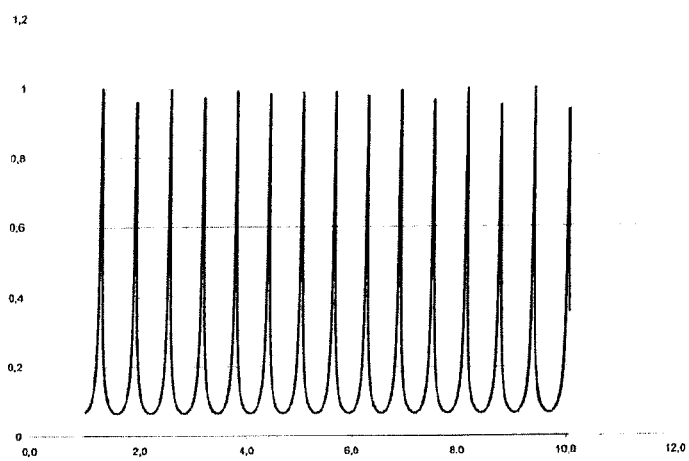

This is exemplified in FIGS. 3A-C, in which is shown examples of amplitude variations of received echo signals as a function of transducer frequency. FIG. 3A shows a graph in a system wherein a contact layer of thickness 0.2 mm is used. The y-axis represents the amplitude of the echoed signal being received by the transducer), and the x-axis represents transducer transmitting frequency in MHz. As can be seen from the figure, there are four peaks at approx. 2.5, 5, 7.5 and 10 MHz at which the received echo signal amplitude is high. Furthermore, as also can be shown in the figure, the reflected amplitude in most part of the spectrum is 0.1 or less of the peak amplitude. According to invention, it is ensured that a high reflected amplitude is received in the transducer by ensuring that a frequency resulting in high received signal power is selected. This can, for example, be accomplished by performing measurements for a number of different (i.e. distinct) fixed frequencies and then compare the results whereby a frequency resulting in a high echo signal amplitude can be selected. The measurement frequencies can, e.g. be a range (or a subrange of) 2-50 MHz.

Consequently, the present invention eliminates the drawback of using a contact layer of a resilient material between transducer and the object to be measured to a large extent. A transducer is in general capable performing a large number of measurements during one single second, e.g. thousands of measurements or more, and thus a large number of frequencies can initially be tested in a relatively short period of time so that a suitable transmit frequency then can be selected for actual measurements.

In general, the location of the peaks of FIG. 3A will vary in dependence of the particular contact layer being tested, and also with the particular object being measured. Further, according to the present invention, measurements of two objects looking identical to the eye are likely to result in different transmit frequencies. Therefore, when using the present invention in e.g. a fastener tightening tool the frequency measurement is preferably performed for each fastener to be fastened. In this way, it can always be ensured that the actual measurement is performed using a transmit frequency that provides an echo signal having good signal quality. It is, however, likely that measurement of similar objects, e.g. fasteners of the same dimension, will result in optimal frequencies being relatively close to each other. Therefore, if e.g. a fastener tightening tool is to be used for tightening a large number of (substantially) identical fasteners, the device can be set to test transducer frequencies in a relatively narrow range, thereby rendering the tool ready for tightening even more quickly.

As was mentioned above, the optimum measurement frequencies depend on the properties of the contact layer as well as the objects to be measured. The frequency dependency on the thickness of the contact layer is exemplified in FIG. 3B in which is shown a graph similar to the one in FIG. 3A, however with the difference that the contact layer has a thickness of 0.4 mm instead. As can be seen, there are a larger number of peaks but the peaks are also narrower. In FIG. 3C is shown a similar example for a contact layer having thickness 0.8 mm, and as can been seen the number of peaks has increased even further while at the same time being even narrower.

Apart from material thickness, the frequency peaks will be dependent on, e.g. the transmittance of the material and the sound propagation speed through the material.

The present invention consequently makes it possible to perform quality measurements of objects without a need to use glycerol, glue or otherwise secure a transducer to the object to be measured. The invention therefore has the advantage that it allows an ultrasonic measurement device to be built into e.g. a fastener tightening tool and allow measurement during ongoing fastening. The invention further has the advantage that the actual tightening force can be very accurately measured also in fastening processes using very fast tools. If the actual tightening force can be accurately measured, considerable material savings can be made, since fasteners of one or even two steps smaller dimension often can be used if it can be ensured that the desired tightening force is actually achieved.

Figure 4:
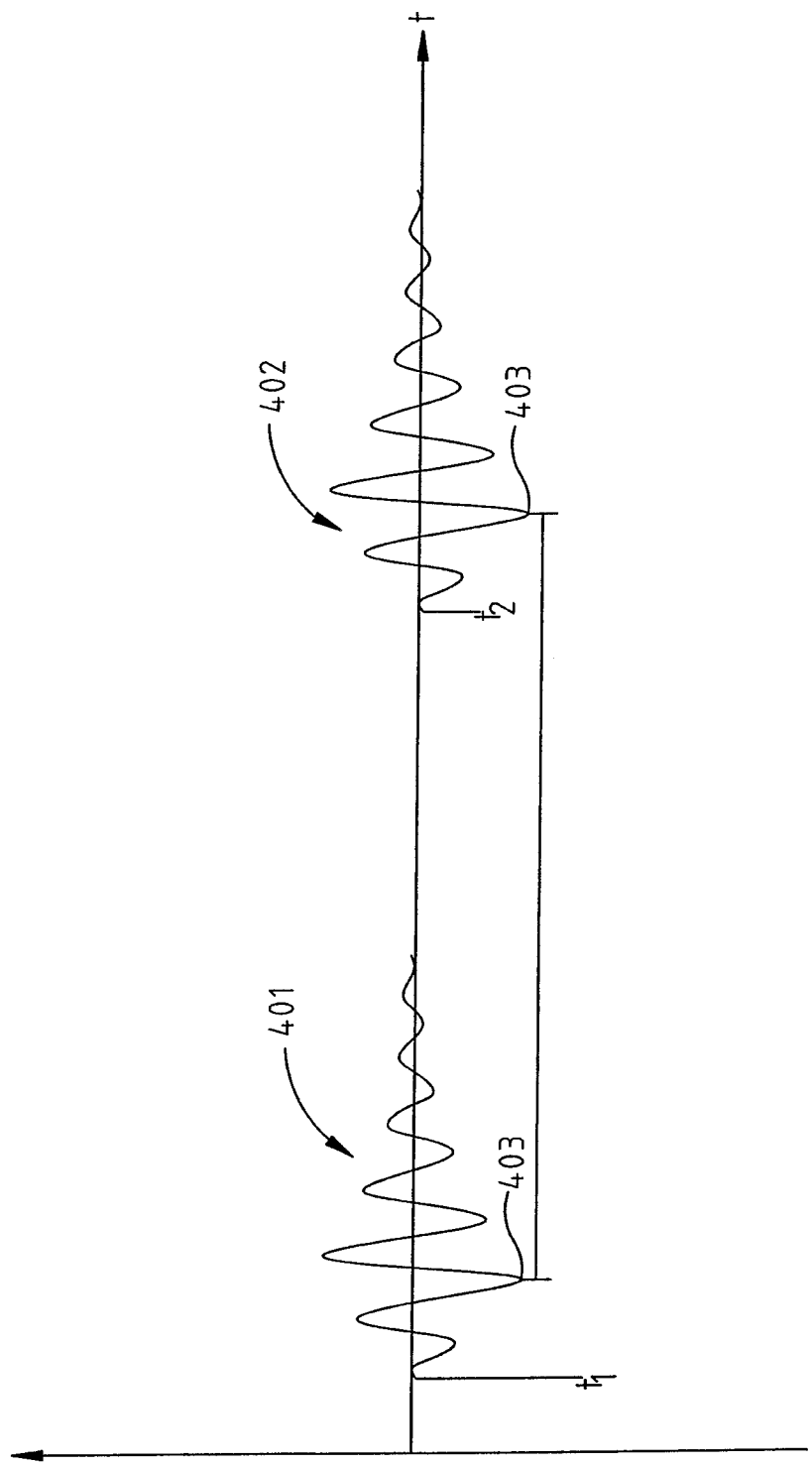
FIG. 4 shows an exemplary ultrasonic measurement signal.

With regard to the signal processing being used once the transmitted ultrasonic echo signal has reached the transducer, this signal processing can be accomplished in any suitable manner. One relatively simple method of accomplishing this signal processing is shown in FIG. 4, in which a time diagram over a transmitted transducer signal and the reflected echo is schematically shown. This particular method is known in the art and consists of transmitting a short pulse or burst at t=t1, in this case consisting of four periods 401. At t=t2 the echo 402 of the transmitted signal is received by the transducer. The shape of the transmitted signal, and thereby the echo signal, is a consequence of the dynamic properties of the transducer, and this effect can be used by performing measurement, e.g. on the negative peak having the largest amplitude (indicated at 403 in the figure). The time period Δt between the largest negative peak in the transmitted signal 401 and the corresponding received peak can then be used to determine e.g. a thickness of the material being tested. If a fastener is being measured the time period Δt is thus dependent on the length of the fastener, and as the fastener is being tightened and thereby elongated, this time period Δt will change and the actual elongation during the fastening process thereby possible to calculate from the difference in Δt. Although this method provides a simple way of measuring e.g. fastener elongation and thereby allows accurate determination of the tightening force, it may still impose ambiguities in the measurement result. For example, if the fastener is not correctly aligned with the fastening tool, the signal shape can be distorted so that the highest peak of the reflected signal no longer corresponds to the highest peak of the transmitted signal, thereby imposing a measurement error of one or more periods of the signal.

According to the present invention, it is also provided a measurement method that overcomes such drawbacks.

Figure 5:
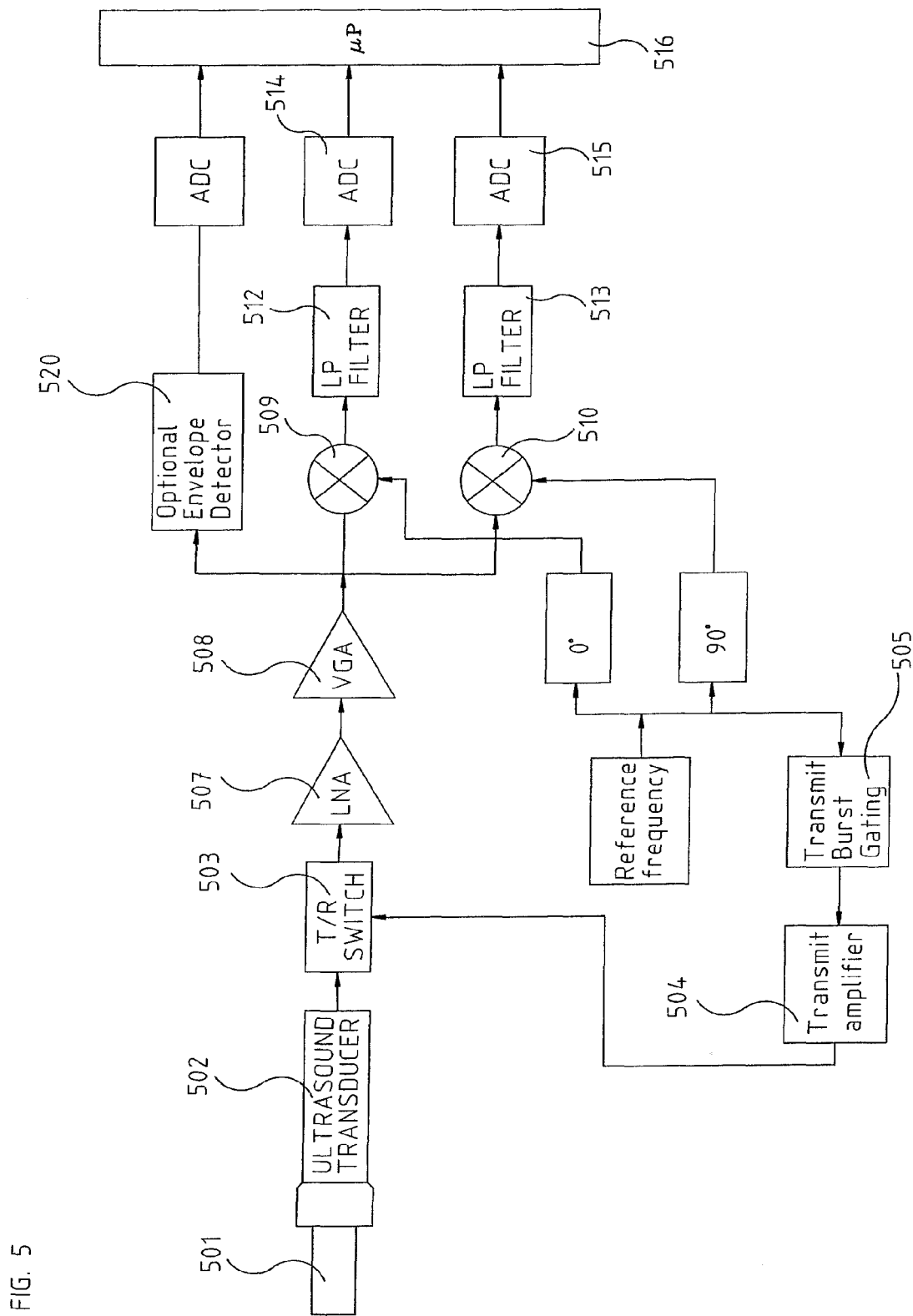
FIG. 5 shows an exemplary signal detection device according to the present invention.

An exemplary embodiment of a measurement method according to the present invention is shown in FIG. 5. The measurement method will be described with reference to an exemplary measurement of a fastener 501. The measurement method that will be described in the following is suitable for use together with the above described frequency selection method, but can also be used in connection with conventional ultrasonic measurements. In the disclosed embodiment, a single transducer 502 is used both for transmission of measurement signals and reception of measurement signals. A transmit/receive switch 503 is used to switch the system between transmit mode and receive mode.

In transmit mode a transmit burst gating device 505 generates a suitable transmit burst of a suitable and fixed frequency, for example by generating a signal of a particular length and frequency. The transmit burst gating device can utilize a suitable frequency generator for generating the desired frequency, and the generated can e.g. be a sine wave signal or a square wave signal or any other type of signal. The transmit signal can also be generated using the reference frequency described below. The generated signal is amplified by a transmit amplifier 504 and then further on to the t/r switch 503, which is set in transmit mode.

The generated transmit burst signal is preferably relatively long, and in principle the only limitation is that it should not be longer than the time it takes for the signal to reach the end of the fastener facing away from the transducer and be echoed back to the transducer, possibly less a suitable guard time, so that the system can be set to measurement mode prior to the arrival of the echoed signal so that the echo signal thereby can be measured. Consequently, when the transmit signal has been transmitted, the t/r switch 503 is set to receive mode and the echo signal received by the transducer 502 is amplified by means of amplifiers 507, 508.

Figure 6A:
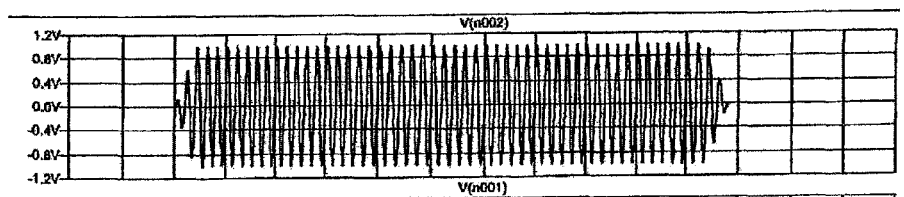
FIGS. 6A-E shows examples of signals occurring in the detection device of FIG. 5.

Consequently, the transmit burst can consist of a considerably larger number of periods as compared to the detection method described in connection with FIG. 4, and an example of the received echo burst is shown in FIG. 6A.

The received echo burst, after the said amplification, is input to an IQ—(In-phase Quadrature) demodulator. In the IQ-demodulator the received signal is split into an I- and Q-channel, respectively, and the channels are multiplied with a reference frequency and the reference frequency phase shifted by 90°, respectively, by means of multipliers 509, 510, i.e. the channels are orthogonal to each other.

Figure 6B:
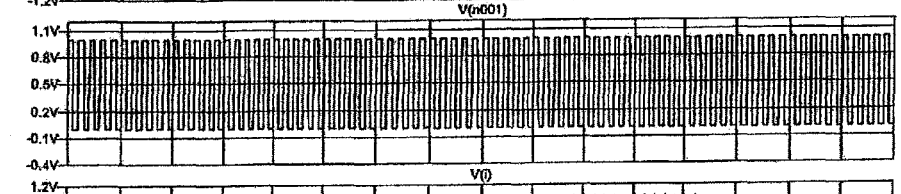

An example of an I-channel reference signal is shown in FIG. 6B. The reference signal is a signal having the same frequency and phase locked to the transmit signal generated by the transmit burst gating device 505, and the Q-channel reference signal consequently being the I-channel reference signal phase shifted 90°.

Figure 6C:
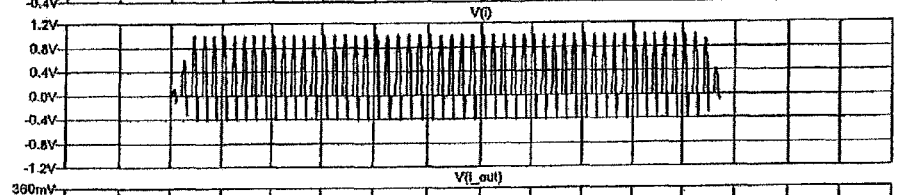
Figure 6D:
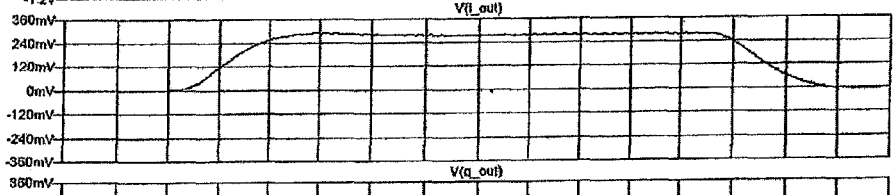
Figure 6E:
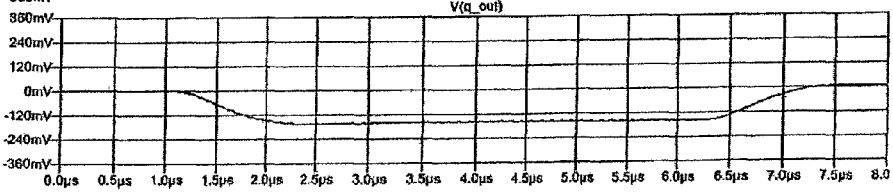

An example of an I-channel demodulator output signal, the signal resulting from the multiplier/mixer 509, is shown in FIG. 6C. The output signals from the multiplier/mixer 509, 510 is then low pass filtered by means of low pass filters 512, 513 so as to generate low pass filtered I- and Q-outputs, respectively. An example of the low pass filtered I-output is shown in FIG. 6D and an example of the low pass filtered Q-output is shown in FIG. 6E. The low pass filtered demodulator output signals are then digitised by means of analogue-to-digital-converters 514 and 515, respectively. The digitised signals are input to a microprocessor performing the actual calculations. The micro processor 516 can calculate a phase difference between the reference signal and the received signal and the reference frequency.

For as long as the fastener is not subject to any elongation, e.g. prior to a fastening process having actually started, this phase difference will remain constant at some value.

However, when a fastening process commences, and thereby also fastener elongation, this phase difference will change due to the fact that the elongation of the fastener will result in a longer signal travel time. By constantly performing measurements according to what has been described above, the phase difference that the received signal undergoes with respect to the transmit signal can be determined by the microprocessor 516 (if the total phase difference exceeds a full period the microprocessor can count the total number of periods that the echo signal undergoes during a fastening process), and when this phase difference has reached a value corresponding to a desired fastener elongation, which in turn corresponds to a desired tightening force, the microprocessor 516 can generate a signal indicating that the tightening should be stopped whereupon the electric motor, such as electric motor 215 of FIG. 2A and thereby the tightening process.

The measurement of the echo signal phase should be repeated at such high repetition frequency (e.g. 1 kHz or higher) during fastening that the echo signal phase difference during fastening can be unambiguously determined between successive measurements.

The measurement method according to the present invention has the advantage that there is no need to have knowledge of the exact shape of the transmitted signal, since no peak measurements are performed. The invention also has the advantage that relatively long burst can be used as transmit signals, thereby improving measurement accuracies. If the same transducer is used both for transmission and reception of the echo signal, the maximum length should not exceed the time it takes for the signal to travel to e.g. the opposite end of the fastener and back. In one embodiment the transmit signal has a length exceeding the time it takes for the signal to travel from the transducer to the opposite end of the object being tested, i.e. where the transmitted signal is reflected.

FIG. 5 also shows a further, optional feature of the signal detector according to the present invention. Apart from the I- and Q-channels, the IQ-demodulator can also comprise an envelope detector 520. The echo signal envelope can be used to obtain a coarse echo delay. The envelope can also be calculated digitally by the measured I- and Q-channel data.

If the disclosed system is to be used for frequency selection according to the above, the system of FIG. 5 can be used e.g. according to the method 700 in FIG. 7.

In step 701 it is determined if a fastener is to be fastened and measurement thereby is to commence. If measurement is to be started, a first transmit frequency f is selected, e.g. by the microprocessor 516. A signal is then transmitted using this frequency, step 702, but instead of determining signal phase, a received signal power, or amplitude, is determined, step 703 and stored, e.g. in a memory. The method then continues to step 704, wherein it is determined whether a signal power (amplitude) peak frequency has been detected, and if not f is changed by a value Δf, and the process is returned to step 702 for a next measurement. This continues until a peak frequency has been determined, or until a frequency having a received (echo) signal power exceeding a desired threshold. In one embodiment, instead of using the exact frequency that results in the peak response, a frequency substantially corresponding to this frequency can be selected, as long as this frequency results in an echo signal of high enough amplitude. This also applies to the threshold solution, in which case a plurality of frequencies may result in an echo signal power of satisfactory amplitude/signal power, and the particular choice among these frequencies may be based on other factors as well. For example, if a wide frequency range is tested, there may even be more than one peak frequencies (see FIGS. 3A-C) in which case there may be other factors affecting the particular choice of frequency.

When a suitable transmit frequency has been determined, step 705, elongation can be measured according to the above.

Although the above described detection method has been described in connection with a fastener tightening tool it is to be appreciated that the described detection method can be used in any situation wherein ultrasonic measurement is to be used, that is the detection method disclosed in FIG. 5 is equally suitable for other kids of ultrasonic measurement, such as measurements for finding inhomogeneities in materials, and also for use with ultrasonic measurement devices wherein the transducer is connected to the object to be measured and frequency detection thereby not being necessary.

Further, although the invention has been described in connection with an electric tightening tool, it is to be understood that it is equally well suited for pneumatic or hydraulic or manual tightening tools, and also electric or pneumatic or hydraulic tools wherein the tightening is accomplished using a pulse tool.

The invention claimed is:

1. An ultrasonic measurement method comprising:
   (a) acoustically coupling an ultrasonic transducer to an object to be measured by means of a resilient material contact layer;
   (b) transmitting, by using said transducer, a plurality of consecutive ultrasonic transmit signals into said object being measured, so that the signals travel from the transducer to an end of the object where the transmit signal is reflected and where a transmit frequency of each of said plurality of transmit signals is distinct from the frequency of the other transmit signals of said plurality of transmit signals;
   (c) selecting, based on received signal echoes, at least one transmit frequency to be used for ultrasonic measurement of said object; and
   (d) transmitting, during measurement, signals into said object using the selected transmit frequency and receiving signal echoes of said transmit signals, wherein said signal echoes are detected by demodulation in two orthogonal channels, so as to allow determination of a phase of a signal echo with respect to the selected transmit signal.

2. The method according to claim 1,
wherein step (b) further comprises:
   selecting a first transmit frequency,
   using said transducer,
   transmitting a first ultrasonic transmit signal having said first transmit frequency, and
   transmitting a second ultrasonic transmit signal having a second transmit frequency; and
wherein step (c) further comprises:
   determining at least one of a signal power and an amplitude of a received signal echo of said first transmit signal,
   determining at least one of a signal power and an amplitude of a received signal echo of said second transmit signal,
   comparing at least one of the determined signal powers and the determined amplitudes of said received signal echoes, and
   selecting the transmit frequency resulting in at least one of a highest signal power and a highest amplitude.

3. The method according to claim 1, further comprising repeating said steps (b)-(d) until a transmit frequency having at least one of a signal power and an amplitude exceeding a first threshold is detected, and selecting a transmit frequency exceeding said first threshold for measurement.

4. The method according to claim 1, further comprising repeating said steps (b)-(d) until a transmit frequency having at least one of a peak signal power and a peak amplitude is detected, and selecting a transmit frequency substantially resulting in said at least one of said peak signal power and said peak amplitude for measurement.

5. The method according to claim 1, wherein said transmit signals each have a distinct and fixed frequency.

6. The method according to claim 1, wherein execution of said steps (a)-(d) is performed under control of a microprocessor in a fastener tightening tool.

7. The method according to claim 6, further comprising:
   prior to tightening of a fastener, determining said transmit frequency, and
   performing real-time ultrasonic measurement during said tightening of said fastener using said fastener tightening tool.

8. The method according to claim 1, wherein said contact layer has a thickness of 0.1-5 mm.

9. The method according to claim 1, wherein said transmit frequencies are in at least a subrange of 2-50 MHz.

10. An ultrasonic measurement device comprising:
    an ultrasonic transducer for coupling to an object to be measured and for transmitting ultrasonic transmit gnals through said object;

receiving means for receiving ultrasonic signal echoes resulting from the ultrasonic transmit signals transmitted by said ultrasonic transducer; and a resilient material contact layer for acoustically coupling said transducer and receiver to the object to be measured, wherein the ultrasonic measurement device is adapted to perform functions comprising:

transmitting, by using said transducer, a plurality of consecutive ultrasonic transmit signals into said object being measured, so that the signals travel from the transducer to an end of the object where the transmit signal is reflected and where a transmit frequency of each of said plurality of transmit signals is distinct from the frequency of the other transmit signals of said plurality of transmit signals;

selecting, based on received signal echoes, at least one transmit frequency to be used for ultrasonic measurement of said object; and transmitting, during measurement, signals into said object using the selected transmit frequency and receiving signal echoes of said transmit signals, wherein said signal echoes are detected by demodulation in two orthogonal channels, so as to allow determination of a phase of a signal echo with respect to the selected transmit signal.

11. The device according to claim 10, wherein said receiving means comprises said transducer.

12. The device according to claim 10, wherein said device comprises a fastener tightening tool.

13. The device according to claim 12, wherein said fastener tightening tool is arranged to measure elongation of a fastener being tightened thereby.

\* \* \* \* \*